United States Patent [19]

Thaisrivongs

[11] Patent Number: 4,705,846

[45] Date of Patent: Nov. 10, 1987

[54] NOVEL RENIN INHIBITING PEPTIDES HAVING A GAMMA LACTAM PSEUDO DIPEPTIDE INSERT

[75] Inventor: Suvit Thaisrivongs, Portage, Mich.

[73] Assignee: The Upjohn Company, Kalamazoo, Mich.

[21] Appl. No.: 844,716

[22] Filed: Mar. 27, 1986

[51] Int. Cl.$^4$ .................... C07K 5/02; C07K 5/06; C07K 5/08; C07K 5/10; C07K 7/06
[52] U.S. Cl. .................... 530/332; 530/331; 530/330; 530/329; 530/328
[58] Field of Search ............... 530/332, 331, 330, 329, 530/328

[56] References Cited

U.S. PATENT DOCUMENTS

| 4,424,207 | 1/1984 | Szelke et al. | 424/177 |
|---|---|---|---|
| 4,470,971 | 9/1984 | Boger et al. | 424/177 |
| 4,477,440 | 10/1984 | Boger et al. | 424/177 |
| 4,477,441 | 10/1984 | Boger et al. | 424/177 |
| 4,478,826 | 10/1984 | Veber et al. | 424/177 |
| 4,478,827 | 10/1984 | Haber et al. | 424/177 |
| 4,479,941 | 10/1984 | Veber et al. | 424/177 |
| 4,485,099 | 11/1984 | Boger et al. | 424/177 |

FOREIGN PATENT DOCUMENTS

| 0045665 | 2/1982 | European Pat. Off. . |
|---|---|---|
| 0045161 | 2/1982 | European Pat. Off. . |
| 0053017 | 6/1982 | European Pat. Off. . |
| 0077028 | 4/1983 | European Pat. Off. . |
| 0077029 | 4/1983 | European Pat. Off. . |
| 0081783 | 6/1983 | European Pat. Off. . |
| 0104041 | 3/1984 | European Pat. Off. . |
| 0111266 | 6/1984 | European Pat. Off. . |
| 0114993 | 8/1984 | European Pat. Off. . |
| 0118223 | 9/1984 | European Pat. Off. . |

OTHER PUBLICATIONS

Holladay et al., "Synthesis of Hydroxyethylene and Ketomethylene Dipeptide Isosteres", Tetrahedron Letters, vol. 24, No. 41, pp. 4401–4404 (1983).

Primary Examiner—Delbert R. Phillips
Attorney, Agent, or Firm—Martha A. Cox

[57] ABSTRACT

The present invention provides novel renin-inhibiting peptides of the formula $X-A_6-B_7-C_8-D_9-E_{10}-F_{11}-G_{12}-H_{13}-I_{14}-Z$, having a lactam pseudo-dipeptide at $C_8-D_9$ positions, X and Z are terminal groups, and the remaining variables are absent or are amino acid residues. Such inhibitors are useful for the diagnosis and control of renin-dependent hypertension.

7 Claims, No Drawings

NOVEL RENIN INHIBITING PEPTIDES HAVING A GAMMA LACTAM PSEUDO DIPEPTIDE INSERT

BACKGROUND OF THE INVENTION

The present invention provides novel compounds. More particularly, the present invention provides novel renin-inhibiting peptide analogs. Most particularly, the present invention provides renin-inhibitory compounds having a lactam pseudo dipeptide at positions 8 and 9 as compared to the renin substrate. The renin inhibitors provided herein are useful for the diagnosis and control of renin-dependent hypertension.

Renin is an endopeptidase which specifically cleaves a particular peptide bond of its substrate (angiotensinogen), of which the N-terminal sequence in equine substrate is for example:

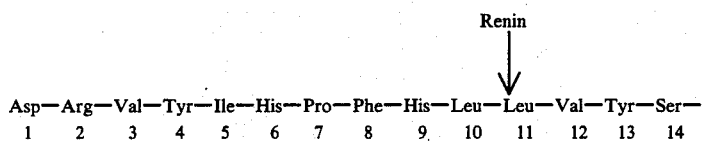

as found by L. T. Skeggs et al, J. Exper. Med. 106, 439 (1957). Human renin substrate has a different sequence as recently discovered by D. A. Tewkesbury et al, Biochem. Biophys. Res. Comm. 99, 1311 (1981). It may be represented as follows:

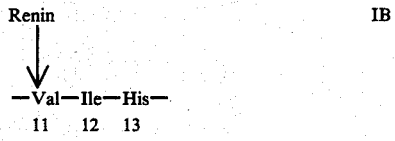

and having the sequence to the left of the arrow ($\downarrow$) being as designated in formula IA above.

Renin cleaves angiotensinogen to produce angiotensin I, which is converted to the potent pressor angiotensin II. A number of angiotensin I converting enzyme inhibitors are known to be useful in the treatment of hypertension. Inhibitors of renin are also useful in the treatment of hypertension.

INFORMATION DISCLOSURE

A number of renin-inhibitory peptides have been disclosed. Thus, U.S. Pat. No. 4,424,207, and European published application Nos. 45,665 and 104,041 disclosed certain peptides with the dipeptide at the 10, 11 position containing an isostere bond. A number of statine derivatives stated to be renin inhibitors have been disclosed, see, e.g., European published application Nos. 77,028; 81,783; and 114,993; and U.S. Pat. Nos. 4,478,826; 4,470,971 and 4,479,941. Terminal disulfide cycles have also been disclosed in renin inhibiting peptides; see, e.g., U.S. Pat. Nos. 4,477,440 and 4,477,441. Aromatic and aliphatic amino acid residues at the 10, 11 position of the renin substrate are disclosed in U.S. Pat. No. 4,478,827. C-terminal amide cycles are disclosed in U.S. Pat. No. 4,485,099. Certain tetrapeptides are disclosed in European publication Nos. 111,266 and 77,027. Further, European published application No. 118,223 discloses certain renin inhibiting peptide analogs where the 10-11 peptide link is replaced by a one to four atom carbon or carbon-nitrogen link. Additionally, Holladay et al., in "Synthesis of Hydroxyethylene and Ketomethylene Dipeptide Isosteres", Tetrahedron Letters, Vol. 24, No. 41, pp. 4401-4404, 1983 disclose various intermediates in a process to prepare stereo-directed "ketomethylene" and "hydroxyethylene" dipeptide isosteric functional groups disclosed in the above noted U.S. Pat. No. 4,424,207.

Additionally, published European Application Nos. 45,161 and 53,017 disclose amide derivatives useful as inhibitors of angiotensin converting enzymes.

SUMMARY OF THE INVENTION

The present invention particularly provides a renin inhibitory peptide of the formula $X-A_6-B_7-C_8-D_9-E_{10}-F_{11}-G_{12}-H_{13}-I_{14}-Z$, wherein X is
  (a) hydrogen,
  (b) $C_1$-$C_5$alkyl

IA (c) $R_5-O-CH_2-C(O)-$,
  (d) $R_5-CH_2-O-C(O)-$,
  (e) $R_5-O-C(O)-$,
  (f) $R_5-(CH_2)_n-C(O)-$,
  (g) $R_4N(R_4)-(CH_2)_n-C(O)-$,
  (h) $R_5-SO_2-(CH_2)_q-C(O)-$,
  (i) $R_5-SO_2-(CH_2)_q-O-C(O)-$, or
  (j) $R_6-(CH_2)_i-C(O)-$;

wherein $A_6$ is absent or a divalent moiety of the formula $XL_1$, $XL_2$, or $XL_{2a}$ wherein $B_7$ is absent or a divalent moiety of the formula $XL_b$ wherein $C_8-D_9$ is $XL_3$ or $XL_{3a}$, or wherein $C_8-D_9$ is a monovalent moiety of the formula $XL_{3b}$ when X, $A_6$, and $B_7$ are absent;

wherein $E_{10}-F_{11}$ is a divalent moiety of the formula $XL_6$, $XL_{6a}$, $XL_{6b}$, $XL_{6c}$, $XL_{6d}$ or $XL_{6e}$;

wherein * indicates an asymmetric center which is either in the R or S configuration;

wherein $G_{12}$ is absent or a divalent moiety of the formula $XL_4$ or $XL_{4a}$;

wherein $H_{13}$ is absent or a divalent moiety of the formula $XL_4$;

wherein $I_{14}$ is absent or a divalent moiety of the formula $XL_5$;

wherein Z is
  (a) $-O-R_{10}$,
  (b) $-N(R_4)R_{14}$, or
  (c) $C_4$-$C_8$cyclic amino;

wherein R is
  (a) isopropyl,
  (b) isobutyl,
  (c) phenylmethyl, or
  (d) $C_3$-$C_7$cycloalkyl;

wherein $R_1$ is
  (a) hydrogen,
  (b) $C_1$-$C_5$alkyl,
  (c) aryl,
  (d) $C_3$-$C_7$cycloalkyl,
  (e) $-$Het,
  (f) $C_1$-$C_3$alkoxy, or
  (g) $C_1$-$C_3$alkylthio;

wherein $R_2$ is
- (a) hydrogen, or
- (b) $-CH(R_3)R_4$;

wherein $R_3$ is
- (a) hydrogen,
- (b) hydroxy,
- (c) $C_1$-$C_5$alkyl,
- (d) $C_3$-$C_7$cycloalkyl,
- (e) aryl,
- (f) —Het,
- (g) $C_1$-$C_3$alkoxy, or
- (h) $C_1$-$C_3$alkylthio;

wherein $R_4$ at each occurrence is the same or different and is
- (a) hydrogen, or
- (b) $C_1$-$C_5$alkyl;

wherein $R_5$ is
- (a) $C_1$-$C_6$alkyl,
- (b) $C_3$-$C_7$cycloalkyl,
- (c) aryl,
- (d) —Het, or
- (e) 5-oxo-2-pyrrolidinyl;

wherein $R_6$ is
- (a) hydrogen,
- (b) $C_1$-$C_5$alkyl,
- (c) $-(CH_2)_p$—aryl,
- (d) $-(CH_2)_p$—Het,
- (e) $-(CH_2)_p$—$C_3$-$C_7$cycloalkyl,
- (f) 1- or 2-adamantyl,
- (g) —S—aryl,
- (h) —S—$C_3$-$C_7$cycloalkyl, or
- (i) —S—$C_1$-$C_6$alkyl;

wherein $R_7$ is
- (a) hydrogen,
- (b) $C_1$-$C_5$alkyl,
- (c) hydroxy,
- (d) amino $C_1$-$C_4$alkyl—,
- (e) guanidinyl $C_1$-$C_3$alkyl—,
- (f) aryl,
- (f) —Het,
- (h) methylthio,
- (i) $-(CH_2)_p$—$C_3$-$C_7$cycloalkyl, or
- (j) amino;

wherein $R_8$ is
- (a) hydrogen,
- (b) $C_1$-$C_5$alkyl,
- (c) hydroxy,
- (d) aryl,
- (e) —Het,
- (f) guanidinyl $C_1$-$C_3$alkyl—, or
- (g) $-(CH_2)_p$—$C_3$-$C_7$cycloalkyl;

wherein $R_9$ is
- (a) hydrogen,
- (b) hydroxy,
- (c) amino $C_1$-$C_4$alkyl—, or
- (d) guanidinyl $C_1$-$C_3$alkyl—;

wherein $R_{10}$ is
- (a) hydrogen,
- (b) $C_1$-$C_5$alkyl,
- (c) $-(CH_2)_n R_{16}$,
- (d) $-(CH_2)_n R_{17}$,
- (e) $C_3$-$C_7$cycloalkyl,
- (f) a pharmaceutically acceptable cation,
- (g) $-CH(R_{25})-CH_2-R_{15}$, or
- (h) $-CH_2-CH(R_{12})-R_{15}$;

wherein $R_{11}$ is —R or —$R_2$;
wherein $R_{12}$ is $-(CH_2)_n-R_{13}$;
wherein $R_{13}$ is
- (a) aryl,
- (b) amino,
- (c) mono-, di or tri-$C_1$-$C_3$alkylamino,
- (d) —Het,
- (e) $C_1$-$C_5$alkyl
- (f) $C_3$-$C_7$cycloalkyl,
- (g) $C_2$-$C_5$alkenyl,
- (h) $C_3$-$C_7$cycloalkenyl,
- (i) hydroxy,
- (j) $C_1$-$C_3$alkoxy,
- (k) $C_1$-$C_3$alkanoyloxy,
- (l) mercapto,
- (m) $C_1$-$C_3$alkylthio,
- (n) —COOH,
- (o) —CO—O—$C_1$-$C_6$alkyl,
- (p) —CO—O—$CH_2$—($C_1$-$C_3$alkyl)—N($C_1$-$C_3$alkyl)$_2$,
- (q) —CO—$NR_{22}R_{26}$;
- (r) $C_4$-$C_7$cyclic amino,
- (s) $C_4$-$C_7$cycloalkylamino,
- (t) guanidyl,
- (u) cyano,
- (v) N-cyanoguanidyl,
- (w) cyanoamino,
- (x) (hydroxy $C_2$-$C_4$alkyl)amino, or
- (y) di-(hydroxy $C_2$-$C_4$alkyl)amino;

wherein $R_{14}$ is
- (a) hydrogen,
- (b) $C_1$-$C_{10}$alkyl,
- (c) $-(CH_2)_n-R_{18}$,
- (d) $-(CH_2)_n-R_{19}$,
- (e) $-CH(R_{25})-CH_2-R_{15}$,
- (f) $-CH_2-CH(R_{12})-R_{15}$,
- (g) (hydroxy $C_1$-$C_8$alkyl), or
- (h) ($C_1$-$C_3$alkoxy)$C_1$-$C_8$alkyl;

wherein $R_{15}$ is
- (a) hydroxy,
- (b) $C_3$-$C_7$cycloalkyl,
- (c) aryl,
- (d) amino,
- (e) mono-, di-, or tri-$C_1$-$C_3$alkylamino,
- (f) mono- or di-[hydroxy $C_2$-$C_4$alkyl]amino,
- (g) —Het,
- (h) $C_1$-$C_3$alkyl—,
- (i) $C_1$-$C_3$alkanoyloxy—,
- (j) mercapto,
- (k) $C_1$-$C_3$alkylthio—,
- (l) $C_1$-$C_5$alkyl,
- (m) $C_1$-$C_7$cyclic amino,
- (n) $C_4$-$C_7$cycloalkylamino,
- (o) $C_1$-$C_5$alkenyloxy,
- (p) $C_3$-$C_7$cycloalkenyl;

wherein $R_{16}$ is
- (a) aryl,
- (b) amino,
- (c) mono- or di-$C_1$-$C_3$alkylamino,
- (d) hydroxy,
- (e) $C_3$-$C_7$cycloalkyl,
- (f) $C_4$-$C_7$cyclic amino, or
- (g) $C_1$-$C_3$alkanoyloxy;

wherein $R_{17}$ is
- (a) —Het,
- (b) $C_2$-$C_5$alkenyl,
- (c) $C_3$-$C_7$cycloalkenyl,
- (d) $C_1$-$C_3$alkoxy,
- (e) mercapto,
- (f) $C_1$-$C_3$alkylthio,
- (g) —COOH, (h) —CO—O—C$_1$-C$_6$alkyl,
(i) —CO—O—CH$_2$—(C$_1$-C$_3$alkyl)—N(C$_1$-C$_3$alkyl)$_2$,
(j) —CO—NR$_{22}$R$_{26}$,
(k) tri-C$_1$-C$_3$alkylamino,
(l) guanidyl,
(m) cyano,
(n) N-cyanoguanidyl,
(o) (hydroxy C$_2$-C$_4$alkyl)amino,
(p) di-(hydroxy C$_2$-C$_4$alkyl)amino, or
(q) cyanoamino;
wherein R$_{18}$ is
(a) amino,
(b) mono-, or di-C$_1$-C$_3$alkylamino,
(c) C$_4$-C$_7$cyclic amino; or
(d) C$_4$-C$_7$cycloalkylamino;
wherein R$_{19}$ is
(a) aryl,
(b) —Het,
(c) tri-C$_1$-C$_3$alkylamino,
(d) C$_3$-C$_7$cycloalkyl,
(e) C$_2$-C$_5$alkenyl,
(f) C$_3$-C$_7$cycloalkenyl,
(g) hydroxy,
(h) C$_1$-C$_3$alkoxy,
(i) C$_1$-C$_3$alkanoyloxy,
(j) mercapto,
(k) C$_1$-C$_3$alkylthio,
(l) —COOH,
(m) —CO—O—C$_1$-C$_6$alkyl,
(n) —CO—O—CH$_2$—(C$_1$-C$_3$alkyl)—N(C$_1$-C$_3$alkyl)$_2$,
(o) —CO—NR$_{22}$R$_{26}$,
(p) guanidyl,
(q) cyano,
(r) N-cyanoguanidyl,
(s) cyanoamino,
(t) (hydroxy C$_2$-C$_4$alkyl)amino,
(u) di-(hydroxy C$_2$-C$_4$alkyl)amino; or
(v) —SO$_3$H;
wherein R$_{20}$ is
(a) hydrogen,
(b) C$_1$-C$_5$alkyl, or
(c) aryl—C$_1$-C$_5$alkyl;
wherein R$_{21}$ is
(a) —NH$_2$, or
(b) —OH;
wherein R$_{22}$ is
(a) hydrogen, or
(b) C$_1$-C$_3$alkyl;
wherein R$_{23}$ is
(a) —(CH$_2$)$_n$—OH,
(b) —(CH$_2$)$_n$—NH$_2$,
(c) aryl, or
(d) C$_1$-C$_3$ alkyl;
wherein R$_{24}$ is
(a) —R$_1$,
(b) —(CH$_2$)$_n$—OH, or
(c) —(CH$_2$)$_n$—NH$_2$;
wherein R$_{25}$ is
(a) hydrogen,
(b) C$_1$-C$_3$ alkyl; or
(c) phenyl—C$_1$-C$_3$ alkyl;
wherein R$_{26}$ is
(a) hydrogen,
(b) C$_1$-C$_3$alkyl, or
(c) phenyl—C$_1$-C$_3$alkyl;
wherein m is one or two;

wherein for each occurrence n is independently an integer of zero to five, inclusive;
wherein p is zero to 2 inclusive;
wherein q is 1 to 5, inclusive;
wherein Q is
(a) —CH$_2$—,
(b) —CH(OH)—,
(c) —O—, or
(d) —S—; and
wherein M is
(a) —CO—, or
(b) —CH$_2$—;
wherein aryl is phenyl or naphthyl substituted by zero to 3 of the following:
(a) C$_1$-C$_3$alkyl,
(b) hydroxy,
(c) C$_1$-C$_3$alkoxy,
(d) halo,
(e) amino,
(f) mono- or di-C$_1$-C$_3$alkylamino,
(g) —CHO,
(h) —COOH,
(i) COOR$_{26}$,
(j) CONHR$_{26}$,
(k) nitro,
(l) mercapto,
(m) C$_1$-C$_3$alkylthio,
(n) C$_1$-C$_3$alkylsulfinyl,
(o) C$_1$-C$_3$alkylsulfonyl,
(p) —N(R$_4$)—C$_1$-C$_3$alkylsulfonyl,
(q) SO$_3$H,
(r) SO$_2$NH$_2$,
(s) —CN, or
(t) —CH$_2$NH$_2$;
wherein —Het is a 5- or 6-membered saturated or unsaturated ring containing from one to three heteroatoms selected from the group consisting of nitrogen, oxygen, and sulfur; and including any bicyclic group in which any of the above heterocyclic rings is fused to a benzene ring, which heterocyclic moiety is substituted with zero to 3 of the following:
(i) C$_1$-C$_6$alkyl,
(ii) hydroxy,
(iii) trifluoromethyl,
(iv) C$_1$-C$_4$alkoxy,
(v) halo,
(vi) aryl,
(vii) aryl C$_1$-C$_4$alkyl—,
(viii) amino,
(ix) mono- or di-C$_1$-C$_4$alkylamino, and
(x) C$_1$-C$_5$alkanoyl;
with the overall provisos that
(1) R$_{18}$ or R$_{19}$ is hydroxy, mercapto, or amino, or a mono-substituted nitrogen containing group bonded through the nitrogen only when n is not one;
(2) R$_{12}$ is —(C$_2$)$_n$—R$_{13}$ and n is zero and both R$_{13}$ and R$_{15}$ are oxygen-, nitrogen- or sulfur-containing substituents bonded through the hetero atom, only when the hetero atom is not also bonded to hydrogen;
(3) R$_{17}$ or R$_{19}$ is —COOH only when n for that moiety is other than zero;
(4) R$_{16}$ or R$_{17}$ is an amino-containing substituent, hydroxy, mercapto, or —Het bonded through the hetero atom only when n for that substituent is an integer from two to five, inclusive;
(5) when R$_{12}$ is —(CH$_2$)$_n$—R$_{13}$ and n is zero, then R$_{13}$ and R$_{15}$ cannot both be —COOH; and (6) $R_{17}$ or $R_{19}$ is —Het, only when —Het is other than cyclic amino;

or a carboxy-, amino-, or other reactive group-protected form thereof;

or a pharmaceutically acceptable acid addition salt thereof.

These compounds are shown in relation to the human renin substrate as follows:

$$\begin{array}{ccccccccc} & 6 & 7 & 8 & 9 & 10 & 11 & 12 & 13 \\ & -\text{His} & \text{Pro} & \text{Phe} & \text{His} & \text{Leu} & \text{Val} & \text{Ile} & \text{His}- \\ X & A_6 & B_7 & C_8 & D_9 & E_{10} & F_{11} & G_{12} & H_{13} & I_{14}\,Z, \end{array}$$

The present invention provides peptide inhibitors of renin which contain modification of positions $C_8$ and $D_9$. These modifications involve the insertion of a lactam moiety at this position.

Examples of pharmaceutically acceptable acid addition salts include: acetate, adipate, alignate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, 3-phenylpropionate, picrate, pivalate, propionate, succinate, tartrate, thiocyanate, tosylate, and undecanoate.

The carbon atoms content of various hydrocarbon-containing moieties is indicated by a prefix designating the minimum and maximum number of carbon atoms in the moiety, i.e., the prefix $(C_i-C_j)$ indicates a moiety of the integer "i" to the integer "j" carbon atoms, inclusive. Thus $(C_1-C_4)$alkyl refers to alkyl of one to 4 carbon atoms, inclusive, or methyl, ethyl, propyl, butyl, and isomeric forms thereof. $C_4-C_7$cyclic amino indicates a monocyclic group containing one nitrogen and 4 to 7 carbon atoms.

Examples of $(C_3-C_{10})$cycloalkyl which include alkyl-substituted cycloalkyl containing a total of up to 10 total carbon atoms, are cyclopropyl, 2-methylcyclopropyl, 2,2-dimethylcyclopropyl, 2,3-dietylcyclopropyl, 2-butylcyclopropyl, cyclobutyl, 2-methylcyclobutyl, 3-propylcyclobutyl, cyclopentyl, 2,2-dimethylcyclopentyl, cyclohexyl, cycloheptyl, cyclooctyl, cyclononyl, cyclodecyl and isomeric forms thereof.

Examples of ary include phenyl, naphthyl, (o-, m-, p-)tolyl, (o-, m-, p-)ethylphenyl, 2-ethyl-tolyl, 4-ethyl-o-tolyl, 5-ethyl-m-tolyl, (o-, m-, or p-)propylphenyl, 2-pyropyl-(o-, m-, or p-)tolyl, 4-isopropyl-2,6-xylyl, 3-propyl-4-ethylphenyl, (2,3,4- 2,3,6- , or 2,4,5-)trimethylphenyl, (o-, m-, p-)fluorophenyl, (o-, m-, or p-trifluoromethyl)phenyl, 4-fluoro-2,5-xylyl, (2,4-, 2,5-, 2,6-, 3,4- or 3,5-)difluorophenyl, (o-, m-, or p-)chlorophenyl, 2-chloro-p-tolyl, (3-, 4-, 5- or 6-)chloro-o-tolyl, 4-chloro-2-propylphenyl, 2-isopropyl-4-chlorophenyl, 4-chloro-3-fluorophenyl, (3- or 4-)chloro-2-fluorophenyl, (o-, m-, or p-)trifluoromethylphenyl, (o-, m-, or p-)ethoxyphenyl, (4- or 5-)chloro-2-methoxyphenyl, and 2,4-dichloro(5- or 6-)methylphenyl, and the like.

Examples of —Het include: 2-, 3-, or 4-pyridyl, imidazolyl, indolyl, $N^{in}$-formyl-indolyl, $N^{in}$-$C_1$-$C_5$alkyl-C(O)-indolyl, [1,2,4]-triazolyl, 2-, 4-, or 5-pyrimidinyl, 2- or 3-theinyl, piperidinyl, pyrryl, pyrrolinyl, pyrrolidinyl, pyrazolyl, pyrazolinyl, pyrazolidinyl, imidazolinyl, imidazolidinyl, pyrazinyl, piperazinyl, pyridazinyl, oxazolyl, oxazolidinyl, isoxazolyl, isoxazolidinyl, morpholinyl, thiazolyl, thiazolidinyl, isothiazolyl, isothiazolidinyl, quinolinyl, isoquinolinyl, benzimidazolyl, benzothiazolyl, benzoxazolyl, furyl, thienyl, and benzothienyl. Each of these moieties may be substituted as noted above.

As would be generally recognized by those skilled in the art of organic chemistry, a heterocycle as defined herein for -Het would not be bonded through oxygen or sulfur or through nitrogen which is within a ring and part of a double bond.

Halo is halogen (fluoro, chloro, bromo, or iodo) or trifluoromethyl.

Examples of pharmaceutically acceptable cations includes: pharmacologically acceptable metal cations, ammonium, amine cations, or quaternary ammonium cations. Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are also within the scope of this invention. Pharmacologically acceptable amine cations are those derived from primary, secondary, or tertiary amines.

The novel peptides herein contain both natural and synthetic amino acid residues. These residues are depicted using standard amino acid abbreviations (see, e.g., IUPAC-IUB Joint Commission on Biochemical Nomenclature (JCBN), "Nomenclature and Symbolish for Amino Acids and Peptides," Eur. J. Biochem. 138:9–37 (1984) unless otherwise indicated.

The renin inhibitors of this invention are useful for treating any medical condition for which it is beneficial to reduce the levels of active circulating renin. Examples of such conditions include renin-dependent hypertension, hypertension, hypertension under treatment with another antihypertensive and/or a diuretic agent, congestive heart failure, angina, and post-myocardial infarction. The renin-angiotension system may play a role in maintenance of intracellular homeostasis: see Clinical and Experimental Hypertension, 86, 1739–1742 (1984) at page 1740 under Discussion.

The compounds of the present invention are preferably orally administered to humans to effect renin inhibitin for the purpose of favorably affecting blood pressure. For this purpose, the compounds are administered from 0.1 mg to 1000 mg per kg per dose, administered from 1 to 4 times daily. Equivalent dosages for other routes of administration are also employed.

The exact dose depends on the age, weight, and condition of the patient and on the frequency and route of administration. Such variations are within the skill of the practitioner or can readily be determined.

The compounds of the present invention may be in the form of pharmaceutically acceptable salts both those which can be produced from the free bases by methods well known in the art and those with which acids have pharmacologically acceptable conjugate bases.

Conventional forms and means for administering renin-inhibiting compounds may be employed and are described, e.g., in U.S. Pat. No. 4,424,207 which is incorporated by reference herein. Likewise, the amounts disclosed in the U.S. Pat. No. 4,424,207 are examples applicable to the compounds of the present invention.

The compounds of the present invention are preferably orally administered in the form of pharmacologically acceptable acid addition salts. Preferred pharmacologically acceptable salts for oral administration include the citrate and aspartate salts, although any pharmacologically acceptable salt is useful in this invention, including those listed above. These salts may be in hydrated or solvated form.

The renin-inhibiting compounds of this invention may be administered in combination with other agents used in antihypertensive therapy such as diuretics, $\alpha$ and/or $\beta$-adrenergic blocking agents, CNS-acting agents, adrenergic neuron blocking agents, vasodilators, angiotensin-converting enzyme inhibitors, and the like as described for example in published European patent application No. 156 318.

The compounds of the present invention are prepared as depicted in the charts and as described more fully in the Preparations and Examples.

In Scheme I, treatment of the racemic $\gamma$-lactones 1 and 3 with lithium thiomethoxide in hexamethylphosphoramide affords the corresponding acids 2 and 4, respectively. The $\gamma$-lactone 1 is obtained from the reaction of benzyl bromide with the lithium salt of $\gamma$-butyrolactone. The $\gamma$-lactone 3 is prepared as described in Preparation 2.

In Scheme II, coupling of the acid 2 and norleucine benzylester 5 gives the amide 6 as a mixture of epimers. Reaction with trimethyloxonium tetrafluoroborate gives the sulfonium salt 7 which is treated with lithium salt of N-methylacetamide to give the desired $\gamma$-lactams 8a and 8b. At this point, the two epimers can be separated by column chromatography on silica gel. The individual benzylesters 8a and 8b are hydrogenolyzed to the corresponding carboxylic acids 9a and 9b, respectively.

The $\gamma$-lactam 13 building block is prepared in an analogous fashion as outlined in Scheme III, starting with the racemic acid 4. In this sequence, the carboxylic acid 13 is isolated as a mixture of epimers.

The reference peptide 16 is prepared as shown in Scheme IV. The previously known amine 14 (H—Leu$\psi$[CHOHCH$_2$]Val—Ile—AMP) is extended on the N-terminus with Boc—norleucine and Boc—phenylalanine successively to give compound 16.

As shown in Scheme V, the separated acids 9a and 9b are individually coupled to the amine 14 to give compounds 17a and 17b, respectively.

The epimeric mixture of acid 13 is coupled to the amine 14 to give compound 18 as shown in Scheme VI. The benzyloxycarbonyl group is removed by hydrogenolysis and the resulting free amine is acetylated to give the peptide 19.

In the statine series, the separated acids 9a and 9b are individually coupled to the previously known amine 20 (H—Sta—Ile—AMP) to give compounds 21a and 21b, respectively, as shown in Scheme VII.

Generally, the renin inhibiting polypeptides may be prepared by either polymer assisted or solution phase peptide synthetic procedures analogous to those described hereinafter or to those methods known in the art. Appropriate protecting groups, reagents, and solvents for both the solution and solid phase methods can be found in "The Peptides: Analysis, Synthesis, and Biology," Vols. 1–5, eds. E. Gross and T. Meienhofer, Academic Press, NY, 1979-1983. Thus, for example, the carboxylic moiety of $N^\alpha$—t—butyloxycarbonyl (Boc)-substituted amino acid derivatives having suitable side chain protecting groups, if necessary, may be condensed with the amino functionality of a suitably protected amino acid, peptide or polymer-bound peptide using a conventional coupling protocol such as dicyclohexylcarbodiimide (DCC) and 1-hydroxybenzotriazole (HOBT) or diethylphosphoryl cyanide (DEPC) and triethylamine (Et$_3$N) in methylene chloride or dimethylformamide. The synthetic procedures used to incorporate the novel moieties herein are analgous to those described, for example, in U.S. Pat. Nos. 4,424,207; 4,470,971; 4,477,440; 4,477,441; 4,478,826, 4,478,827; 4,479,941; and 4,485,099, and copending application Ser. No. 753,198, filed July 9, 1985, now abandoned, and copending application Ser. No. 825,250, filed Feb. 3, 1986, all of which are expressly incorporated by reference herein. See, also, published European patent application Nos. 45,161; 45,665; 53,017; 77,028; 77,029; 81,783; 104,041; 111,266; 114,993; and 118,223.

Following coupling reaction completion, the $N^\alpha$—Boc moiety may be selectively removed with 45% trifluoroacetic acid with or without 2% anisole (v/v) in methylene chloride. Neutralization of the resultant trifluoroacetate salt may be accomplished with 10% diisopropylethylamine or sodium bicarbonate in methylene chloride. In the case of polymer-assisted peptide synthesis, this stepwise, coupling strategy may be partially or completely automated to provide the desired peptide-polymer intermediates. Anhydrous hydrofluoric acid treatment of the peptide-polymer intermediate may then be used to effect simultaneous protecting group removal and cleavage of the peptide from its polymeric support. A notable exception to this includes $N^{in}$—formyl—indolyl-substituted peptides in which the $N^{in}$—formyl—indolyl moiety is stable to TFA or hydrogen fluoride but may be removed by ammonia or sodium hydroxide. Because $N^{in}$—formyl—tryptophane (FTrp) is somewhat unstable to base in synthetic procedures, possibly causing lower yields, it may be desirable in solution phase synthesis to introduce the FTrp-containing moiety late in the synthetic sequence so that it is not exposed to such conditions.

The incorporation of $N^{in}$—formyl—Trp into compounds of the present invention is easily accomplished because of the commercial availability of $N^\alpha$—Boc—$N^{in}$—formyl—Trp—OH. However, the $N^{in}$—formyl moiety may be introduced into indolyl-substituted amino acid derivatives or related compounds by reaction with hydrochloric-formic acid as reported in the literature, see A. Previero et al, Biochim. Biophys. Acta 147, 453 (1967); Y. C. S. Yang et al, Int. J. Peptide Protein Res. 15, 130 (1980).

Generally, methods of alkylation useful in alkylating histidine for use in the present invention are found in Chung, S. T. et al, Can. J. Chem., Vol 55, pp. 906–910 (1977). However it is now found that in the Cheung, S. T. et al, method, it is critical that the reaction conditions for the alkylation of histidine be anhydrous. Further, it is now found also that during work-up instead of adding water directly to the reaction mixture, it is preferred that a buffered aqueous solution be added to the reaction mixture, for example, aqueous sodium or potassium hydrogen sulfate.

Variations in the above description for starting materials, reactants, reaction conditions and required protecting groups to obtain other such N-alkylated compounds are known to an ordinarily skilled chemist or are readily available in the literature.

The compounds of the present invention may be in either free form or in protected form at one or more of the remaining (not previously protected) peptide, carboxyl, amino, hydroxy, or other reactive groups. The protecting groups may be any of those known in the polypeptide art. Examples of nitrogen and oxygen protection groups are set forth in T. W. Greene, Protecting Groups in Organic Synthesis, Wiley, New York, (1981); J. F. W. McOmie, ed. Protective Groups in Organic Chemistry, Plenum Press (1973); and J. Fuhrhop and G. Benzlin, Organic Synthesis, Verlag Chemie (1983). Included among the nitrogen protective groups are t-butoxycarbonyl (Boc), benzyloxycarbonyl, acetyl, allyl, phthalyl, benzyl, benzoyl, trityl and the like.

DESCRIPTION OF THE PREFERRED EMBODIMENTS

The following Preparations and Examples illustrate the present invention.

In the Preparations and Examples below and throughout this document:

Ph is phenyl
DCC is dicyclohexylcarbodiimide
HOBT is 1-hydroxybenzotriazole
BOC is t-butoxycarbonyl
DEPC is diethylphosphoryl cyanide
TFA is trifluoroacetic acid
TEA is triethylamine
M or mol is mole
C. is centigrade
ml is milliliter
THF is tetrahydrofuran
TLC is thin layer chromatography
EtOAc is ethyl acetate
MS is mass spectroscopy
IR is infra red spectra
$^1$H-NMR is nuclear magnetic resonance
CDCl$_3$ is deuteriochloroform
HPLC is high performance liquid chromatography
MPLC is medium pressure liquid chromatography
g. is grams
min. is minute
Me is methyl
AMP is 2-(aminomethyl)pyridinyl
Tos is p-toluenesulfonyl
Bn is benzylester
Bz is benzyl
Cbz is benzyloxycarbonyl.
The wedge-shape line indicates a bond which extends above the plane of the paper relative to the plane of the compound thereon.
The dotted line indicates a bond which extends below the plane of the paper relative to the plane of the compound thereon.
Celite is a filter aid.
RIP means a compound having the formula H—Pro—His—Phe—His—Phe—Phe—Val—Tyr—Lys—OH.2(CH$_3$C(O)OH).X-H$_2$O which is a known renin-inhibiting peptide.
FTrp is N$^{in}$—formyl—Trp.

Preparation 1 2-(2-Methylthioethyl)-dihydrocinnamic acid (2). Refer to Scheme I.

A mixture of 1.0326 g of 2-benzyl-γ-butyrolactone (1) and 0.64 g of lithium thiomethoxide in 5 ml of hexamethylphosphoramide is allowed to stir at room temperature. After 2 days, the reaction mixture is taken up in 50 ml of water and then extracted with three 30 ml portions of dichloromethane. The aqueous phase is acidified (methyl orange as indicator) with concentrated hydrochloric acid. The resulting mixture is extracted with three 30 ml portions of ether. The combined ethereal phases are washed with three 20 ml portions of water. The organic phase is then dried with magnesium sulfate and then concentrated to give 1.25 g of the title product 2.

Physical characteristics are as follows:
$^1$H-NMR (δ, CDCl$_3$): 7.24, 2.01.

Preparation 2
α-Benzyl-α-benzyloxycarbonylamino-γ-butyrolactone (3). Refer to Scheme I.

To a mixture of 3.84 g of α-amino-γ-butyrolactone hydrogenbromide in 40 ml of dichloromethane is added 2.15 ml of benzaldehyde, followed by 5.9 ml of triethylamine and excess magnesium sulfate. After stirring at room temperature for 20 hours, the mixture is filtered and the filtrate concentrated. A 200 ml portion of ether is added and the resulting suspension filtered. The filtrate is washed with 50 ml of saturated aqueous sodium chloride. The aqueous phase is extracted with two 100 ml portions of ether. The combined organic phase is dried (magnesium sulfate), filtered, and then concentrated. The residue is evaporatively distilled at 0.05 mmHg (Krugelröhr oven 200°–250° C.) to give 3.5 g of N-benzylidene-α-amino-γ-butyrolactone as an oil which solidifies on storage in a freezer:

$^1$H-NMR (δ, CDCl$_3$): 2.9, 4.3, 7.35, 7.7, 8.3.

To a stirred solution of 2.8 ml of diisopropylamine in 12 ml of tetrahydrofuran at −78° C. under argon is added 11.7 ml of n-butyllithium in hexane. After 15 min, a solution of 3.16 g of N-benzylidene-α-amino-γ-butyrolactone in 10 ml of tetrahydrofuran at −78° C. under argon is cannulated into the stirred reaction mixture. After 15 min, 2.14 ml of benzyl bromide is added. After 5 min, the reaction mixture is allowed to stir at room temperature for 24 hours. It is then cooled in an ice bath and 20 ml of 10% aqueous hydrogen chlorine is added. After stirring at room temperature for 1 hour, it is recooled in an ice bath and an excess of saturated aqueous sodium bicarbonate is slowly added. The resulting mixture is added to 200 ml of dichloromethane and washed with 50 ml of saturated aqueous sodium bicarbonate. The aqueous phase is extracted with three 100 ml portions of dichloromethane. The combined organic phae is dried (magnesium sulfate), filtered, and then concentrated. The resulting residue is flash-chromatographed on silica gel with ethyl acetate to 5% methanol in ethyl acetate to give 1.6 g of α-benzyl-α-amino-γ-butyrolactone as a yellow oil:

$^1$H-NMR (δ, CDCl$_3$): 1.56, 2.81, 3.03, 7.2.

To a stirred solution of 1.55 g of α-benzyl-α-amino-γ-butyrolactone in 16 ml of tetrahydrofuran is added 2.0 g of powdered sodium carbonate, followed by 1.27 ml of benzylchloroformate. After stirring at room temperature for 18 hours, water is added to dissolve the salt and the resulting mixture is diluted with 100 ml of ethyl acetate. It is washed with 50 ml of saturated aqueous sodium chloride. The aqueous phase is extracted with two 50 ml portions of ethyl acetate. The combined organic phase is dried (magnesium sulfate), filtered, and then concentrated. The residue is passed through 20 g of silica gel with ethyl acetate, and the filtrate concentrated to the title product as a white solid, 2.6 g.

Physical characteristics are as follows:
$^1$H-NMR (δ, CDCl$_3$): 2.67, 2.97, 3.2, 3.44, 4.15, 5.10, 5.34, 7.26, 7.34.
Anal. Found: C. 70.29; H, 5.96; N, 4.13.
MS M/Z 234, 190, 175, 174, 91.

Preparation 3
2-Benzyl-N-benzyloxycarbonyl-DL-methionine (4). Refer to Scheme I.

A mixture of 2.475 g of the γ-lactone 3 of Preparation 2 and 540 mg of lithium thiomethoxide in 8 ml of hexamethylphosphoramide is allowed to stand at room temperature for 4 days. It is then added to 150 ml of dichloromethane and 50 ml of saturated aqueous sodium chloride. To this vigorously-stirred mixture is added 10% aqueous hydrochloric acid (methyl orange indicator) until acidic. The organic phase is further washed with 50 ml of saturated aqueous sodium chloride. The aqueous phases are extracted with the same two 60 ml portions of dichloromethane. The combined organic phase is dried with magnesium sulfate, filtered, and then concentrated. The residue is taken up in 200 ml of water and the aqueous phase extracted with three 200 ml portions of ether. The combined organic phase is dried with magnesium sulfate, filtered, and then concentrated to give 2.5 g of the title product 4.

Physical characteristics are as follows:
$^1$H-NMR (δ, CDCl$_3$): 6.8–7.4, 5.5, 5.1, 3.6, 3.1, 2.1.

Preparation 4
N-[2-(2-methylthioethy)-dihydrocinnamyl]-L-norleucyl-benzylester (6). Refer to Scheme II To a stirred solution of 5.54 mmol of the acid 2 of Preparation 1, 6.1 mmol of L-norleucyl-benzylester (5) (tosyl salt in dichloromethane is washed with saturated aqueous sodium bicarbonate and dried over magnesium sulfate), 0.75 g of HOBT in 50 ml of dichloromethane is added 1.25 g of DCC. After 14 hours, the reaction mixture is filtered and the filtrate washed with aqueous sodium bicarbonate. The organic phase is dried with magnesium sulfate and then concentrated. The residue is chromatographed on silica gel to give 2 g of the title product 6.

Physical characteristics are as follows:
$^1$H-NMR (δ, CDCl$_3$): 7.3, 5.9, 5.22, 5.05, 2.01.
IR (cm$^{-1}$, mull): 3312, 1724, 1639.
$[α]_D = -14°$ (c=1.01, chloroform).
MS: 427.2176 (found).
Anal. Found: C, 70.16; H, 7.71; N, 3.28.

Preparation 5
3R-Benzyl-2-oxo-1-pyrrolidine-2S-hexanoic acid, benzyl ester (8a) and 3S-benzyl-2-oxo-1-pyrrolidine-2S-hexanoic acid, benzyl ester (8b). Refer to Scheme II A mixture of 747 mg of the amide 6 of Preparation 4 and 272 mg of trimethyloxonium tetrafluoroborate in 7 ml of dichloromethane is allowed to stir at room temperature for 2 hours. The solution is then concentrated and dried.

A solution of 190 mg of N-methyl-acetamide in 15 ml of tetrahydrofuran at 0° C. under argon is added 1.75 ml of lithium hexamethyldisilazide. After 30 min, the reaction mixture is partitioned between ethyl acetate and saturated aqueous sodium bicarbonate. The organic phase is dried with magnesium sulfate and then concentrated. The residue is chromatographed on silica gel MPLC with 10% to 15% ethyl acetate in hexane to give 221 mg and 342 mg, respectively, of the title products 8a and 8b.

Physical characteristics are as follows:
Title product 8a:
$^1$H-NMR (δ, CDCl$_3$): 7.3, 7.2, 5.2.
IR (cm$^{-1}$, neat): 1740, 1692.
$[α]_D = +22°$ (c=0.525, chloroform).
MS: 379.2146 (found).
Anal. Found: C, 75.10; H, 7.74; N, 3.63.
Title product 8b:
$^1$H-NMR (δ, CDCl$_3$): 7.3, 7.2, 5.2.
IR (cm$^{-1}$, neat): 1740, 1691.
$[α]_D = -60°$ (c=0.658, chloroform).
MS: 379.2146 (found).
Anal. Found: C, 75.31; H, 7.76; N, 3.32.

Preparation 6
3R-Benzyl-2-oxo-1-pyrrolidine-2S-hexanoic acid (9a). Refer to Scheme II A suspension of 152 mg of the benzyl ester 8a of Preparation 5 and 15 mg of 10% pallidium on activated charcoal in 3 ml of methanol is stirred under hydrogen at room temperature for 2 hours. The mixture is filtered and residue washed with methanol. The filtrate is combined and concentrated to give 107 mg of the title product 9a as a white solid.

Preparation 7
3S-Benzyl-2-oxo-1-pyrrolidine-2S-hexanoic acid (9b). Refer to Scheme II A suspension of 272 mg of the benzyl ester 8b of Preparation 5 and 25 mg of 10% palladium on activated charcoal in 3 ml of methanol is stirred under hydrogen at room temperature for 2 hours. The mixture is filtered and the residue washed with more methanol. The filtrate is concentrated to give 206 mg of the title product 9b as a thick oil.

Preparation 8
2-Benzyl-N-benzyloxycarbonyl-DL-methionyl-L-norleucyl-benzylester (10). Refer to Scheme III To a stirred solution of 1.43 mmol (from 562 mg of L-norleucyl-benzylester-p-toluenesulfonic acid/methylene chloride/aqueous sodium bicarbonate) of L-norleucyl-benzylester (5), 590 mg of the acid 4 of Preparation 3 and 210 mg of HOBT in 20 ml of methylene chloride is added 320 mg of DCC. After 6 hours, the mixture is filtered and the filtrate partitioned between methylene chloride and saturated aqueous sodium bicarbonate. The organic phase is dried with magnesium sulfate and then concentrated. The residue is triturated with EtOAc and then filtered. The concentrated filtrate is chromatographed on Lobar size B column with 15% EtOAc in hexane to give the title product 10 as a white solid, 713 mg.

Physical characteristics are as follows:
$^1$-NMR (CDCl$_3$) shows approximately equal mixture of two diastereomers;
IR (cm$^{-1}$, mull): 1744, 1721, 1651.
$[α]_D = -7°$ (c=0.79, chloroform).
Anal. Found: C, 68.78; H, 6.92; N, 4.78; S, 5.88.

Preparation 9 (R and S)-3-benzyl-3-benzyloxycarbonylamino-2-oxo-1-pyrrolidine-2S-hexanoic acid, benzyl ester (12). Refer to Scheme III A mixture of 656 mg of the amide 10 of Preparation 8 and 180 mg of trimethyloxonium tetrafluoroborate in 4.5 ml of methylene chloride is allowed to stir at room temperature for 90 min. It is then concentrated.

To a stirred solution of 125 mg of N-methyl-acetamide in 10 ml of THF at 0° C. is added 1.1 ml of lithium hexamethyldisilazide in THF. After 15 min a solution of the above residue in 5 ml of THF is added. After 1 hour, the reaction mixture is partitioned between methylene chloride and saturated aqueous sodium bicarbonate. The organic phase is dried with magnesium sulfate and then concentrated. The residue is flash-chromatographed on silica gel with 25% EtOAc in hexane to give 384 mg of the title product 12.

Physical characteristics are as follows:

$^1$H-NMR (CDCl$_3$) shows approximately equal mixture of two diastereomers.

IR (cm$^{-1}$, neat): 1738, 1697.

$[\alpha]_D = -26°$ (c=0.789, chloroform).

MS: 529.2695 (found).

Anal. Found: C, 72.21; H, 6.92; H, 5.02.

Preparation 10 (R and S)-3-benzyl-3-benzyloxycarbonylamino-2-oxo-1-pyrrolidine-2S-hexanoic acids (13). Refer to Scheme III.

To a stirred solution of 326 mg of the ester 12 of Preparation 9 in 2 ml of THF is added 1 ml of 1M aqueous sodium hydroxide and small amount of methanol to obtain a clear homogeneous solution. After 4 hours, THF is removed on a rotary evaporator. The aqueous phase is extracted with ether and then acidified with concentrated hydrochloric acid (methyl orange). Extractions with methylene chloride gives the title product 13 (233 mg).

Physical characteristics are as follows:

$^1$H-NMR (CDCl$_3$) shows approximately equal mixture of two diastereomers.

IR (cm$^{-1}$, mull): 1720, 1643.

$[\delta]_D = -29°$ (c=0.405, chloroform).

MS: 439.2211 (found).

Anal. Found: C, 67.53; H, 6.96; N, 6.17.

Preparation 11
N-tert-butyloxycarbonyl-L-norleucyl-5S-amino-4S-hydroxy-2S-isopropyl-7-methyl-octanoyl-L-isoleucyl-2-pyridylmethylamide (15). Refer to Scheme IV To a stirred solution of 33.7 mg of Boc—Nle[N-tert-butyloxycarbonyl-L-norleucine] and 33.9 mg of 5S-amino-4S-hydroxy-2S-isopropyl-7-methyl-octanoyl-L-isoleucyl-2-pyridiylmethyl-amide (14) in 1 ml of dichloromethane is added 0.02 ml of TEA and 0.02 ml of DEPC. After 14 hours, the suspension is partitioned between dichloromethane and saturated aqueous sodium bicarbonate. The organic phase is dried with magnesium sulfate and then concentrated. The residue is chromatographed on silica gel with methylene chloride to 10% methanol in methylene chloride to give 46 mg of the title product 15.

Preparation 12
N-tert-butyloxycarbonyl-L-phenylalanyl-L-norleucyl-5S-amino-4S-hydroxy-2S-isopropyl-7-methyl-octanoyl-L-isoleucyl-2-pyridylmethylamide (16). Refer to Scheme IV The peptide 15 of Preparation 11 in 0.5 ml of dichloromethane and 0.5 ml of TFA is allowed to stir at room temperature for 30 min. The concentrated residue is partitioned between dichloromethane and saturated aqueous sodium bicarbonate. The organic phase is dried with magnesium sulfate and concentrated. The residue is dissolved in 1 ml of dichloromethane and 25 mg of N-tert-butyloxycarbonyl-L-phenylalanine is added, followed by 0.015 ml of TEA and 0.015 ml of DEPC. After 14 hours, the concentrated mixture is chromatographed on silica gel with 1% to 10% methanol in methylene chloride to give 50 mg of the title product 16.

Physical characteristics are as follows:

HPLC (4:1=methanol:aqueous pH 3 phosphate buffer): 6 min (retention time).

MS: 795.5395 (found).

EXAMPLE 1
3R-Benzyl-2-oxo-1-pyrrolidine-2S-hexanoyl-5S-amino-4S-hydroxy-2S-isopropyl-7-methyl-octanoyl-L-isoleucyl-2- pyridylmethylamide (17a). Refer to Scheme V To a stirred mixture of 20 mg of the acid 9a of Preparation 6, 20 mg of 5S-amino-4S-hydroxy-2S-isopropyl-7-methyl-octanoyl-L-isoleucyl-2-pyridylmethyl-amide (14) and 0.01 ml of TEA in 1 ml of dichloromethane is added 0.01 ml of DEPC. After 14 hours, the concentrated mixture is chromatographed on silica gel with 1% to 10% methanol in methylene chloride to give 26 mg of the title product 17a.

Physical characteristics are as follows:

HPLC (4:1=methanol:aqueous pH 3 phosphate buffer): 7.2 min (retention time).

MS: 706.4882 (found).

EXAMPLE 2
3S-Benzyl-2-oxo-1-pyrrolidine-2S-hexanoyl-5S-amino-4S-hydroxy-2S-isopropyl-7-methyl-octanoyl-L-isoleucyl-2-pyridylmethylamide (17b). Refer to Scheme V To a stirred mixture of 20 mg of the acid 9b of Preparation 7, 20 mg of 5S-Amino-4S-hydroxy-2S-isopropyl-7-methyl-octanoyl-L-isoleucyl-2-pyridylmethyl-amide (14) and 0.01 ml of TEA in 1 ml of dichloromethane is added 0.01 ml of DEPC. After 14 hours, the concentrated mixture is chromatographed on silica gel with 1% to 10% methanol in methylene chloride to give 30 mg of the title product 17b.

Physical characteristics are as follows:

HPLC (4:1=methanol:aqueous pH 3 phosphate buffer): 6 min (retention time).

MS: 706.4917 (found).

EXAMPLE 3
(R and S)-3-benzyl-3-benzyloxycarbonylamino-2-oxo-1-pyrrolidine-2S-hexanoyl-5S-amino-4S-hydroxy-2S-isopropyl-7-methyl-octanoyl-L-isoleucyl-2-pyridylmethylamide (18). Refer to Scheme VI To a stirred solution of 57.7 mg of 5S-amino-4S-hydroxy-2S-isopropyl-7-methyl-octanoyl-L-isoleucyl-2-pyridylmethyl-amide (14), 75 mg of the acid 13 of Preparation 10 and 0.025 ml of triethylamine in 1.5 ml of dichloromethane is added 0.025 ml of DEPC. After 4 hours, the reaction mixture is concentrated and the residue is chromatographed on silica gel with 5% methanol in dichloromethane to give 117 mg of the title product 18.

Physical characteristics are as follows:

HPLC (4:1=methanol:aqueous pH 3 phosphate buffer): 8 and 10.4 min (retention time).

MS: 855.5422 (found).

EXAMPLE 4

(R and S)-3-benzyl-3-acetylamino-2-oxo-1-pyrrolidine-2S-hexanoyl-5S-amino-4S-hydroxy-2S-isopropyl-7-methyl-octanoyl-L-isoleucyl-2-pyridylmethylamide (19). Refer to Scheme VI A mixture of 105 mg of the peptide 18 of Example 3 and 20 mg of 10% palladium/carbon in 3 ml of methanol is allowed to stir under hydrogen for 2 hours. The mixture is filtered through Celite and then concentrated to give 89 mg. The material is re-hydrogenated in 5 ml of methanol (0.2 ml of acetic acid) and 20 mg of 10% palladium/carbon under 50 psi of hydrogen. After 1 day, the mixture is filtered through Celite and then concentrated. The residue is partitioned between methylene chloride and saturated aqueous sodium bicarbonate. The organic phase is dried with magnesium sulfate and then concentrated. The residue is chromatographed on silica gel with 5% methanol in methylene chloride to 5% methanol (saturated with ammonia) in methylene chloride to give 37.4 mg of (R and S)-3-benzyl-3-amino-2-oxo-1-pyrrolidine-2S-hexanoyl-5S-amino-4S-hydroxy-2S-isopropyl-7-methyl-octanoyl-L-isoleucyl-2-pyridylmethylamide.

To a stirred solution of 37.4 mg of (R and S)-3-benzyl-3-amino-2-oxo-1-pyrrolidine-2S-hexanoyl-5S-amino-4S-hydroxy-2S-isopropyl-7-methyl-octanoyl-L-isoleucyl-2-pyridylmethylamide, 0.004 ml of acetic acid and 0.01 ml of TEA in 0.5 ml of methylene chloride is added 0.01 ml of DEPC. After 3 hours, the concentrated reaction mixture is chromatographed on silica gel with EtOAc to 4% methanol in EtOAc to give the title product 19.

Physical characteristics are as follows:

HPLC (4:1=methanol:aqueous pH 3 phosphate buffer): 4.7 and 7.2 min (retention time).

MS: 763.5147 (found).

EXAMPLE 5

3R-benzyl-2-oxo-1-pyrrolidine-2S-hexanoyl-4S-amino-3S-hydroxy-6-methyl-heptanoyl-L-isoleucyl-2-pyridyl-methylamide (21a). Refer to Scheme VII To a stirred solution of 43.6 mg of the acid 9a of Preparation 6 57 mg of 4S-amino-3S-hydroxy-6-methyl-heptanoyl-L-isoleucyl-2-pyridylmethylamide (20), 0.025 ml of TEA in 1 ml of methylene chloride is added 0.025 ml of DEPC. After 14 hours, the reaction mixture is concentrated and residue chromatographed on silica gel with 1% to 5% methanol in methylene chloride to give 75 mg of the title product 21a.

Physical characteristics are as follows:

HPLC (3:1=methanol:aqueous pH 3 phosphate buffer): 8.9 min (retention time).

MS: 650.4270 (found).

EXAMPLE 6

3S-benzyl-2-oxo-1-pyrrolidine-2S-hexanoyl-4S-amino-3S-hydroxy-6-methyl-heptanoyl-L-isoleucyl-2-pyridyl-methylamide (21b). Refer to Scheme VII To a stirred solution of 134.6 mg of the acid 9b of Preparation 7, 176 mg of 4S-amino-3S-hydroxy-6-methyl-heptanoyl-L-isoleucyl-2-pyridylmethylamide (20) and 0.07 ml of TEA in 2 ml of methylene chloride is added 0.07 ml of DEPC. After 14 hours, the mixture is concentrated and the residue chromatographed on silica gel with 1% to 5% methanol in methylene chloride to give 255 mg of the title product 21b.

Physical characteristics are as follows:

HPLC (3:1=methanol:aqueous pH 3 phosphate buffer): 9.1 min (retention time).

MS: 650.4315 (found).

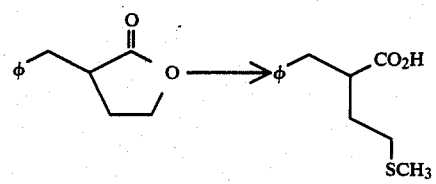

Scheme I

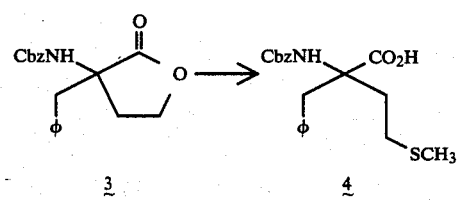

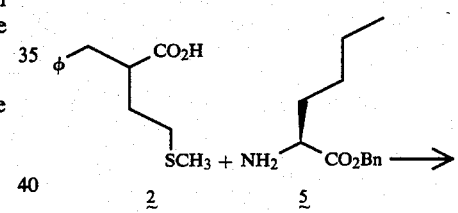

Scheme II

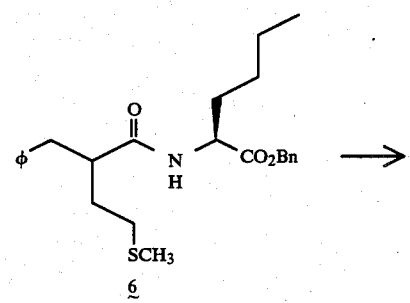

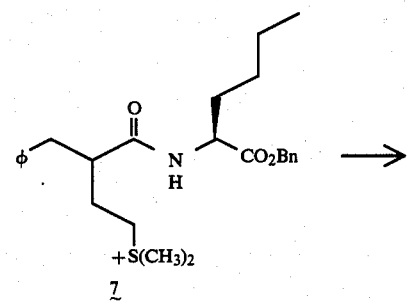

4,705,846
19
-continued
Scheme II
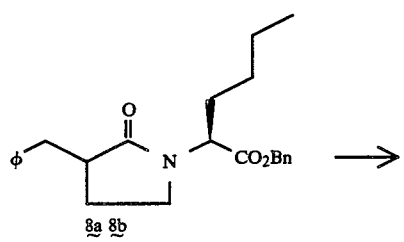
8a 8b
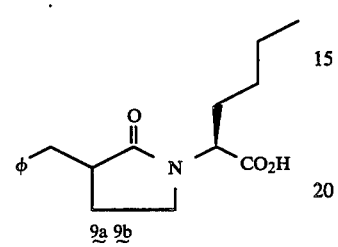
9a 9b
Scheme III
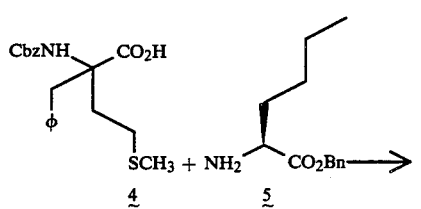
4    5
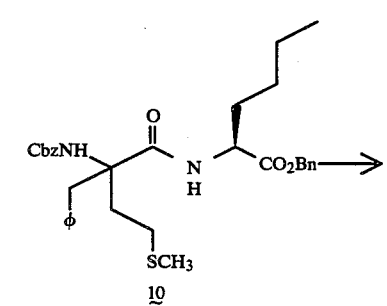
10
20
-continued
Scheme III
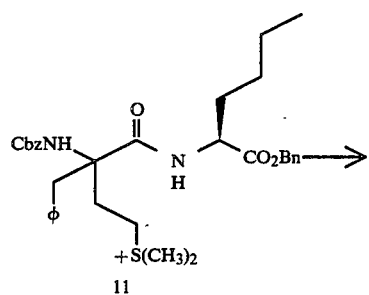
11
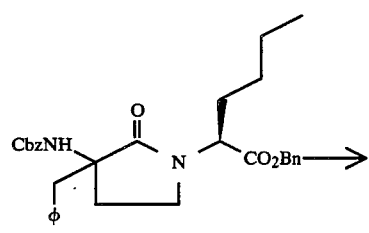
12
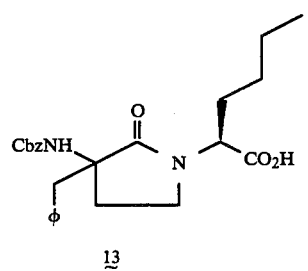
13
Scheme IV
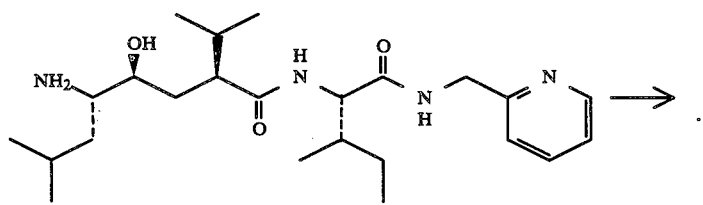
14

-continued
Scheme IV
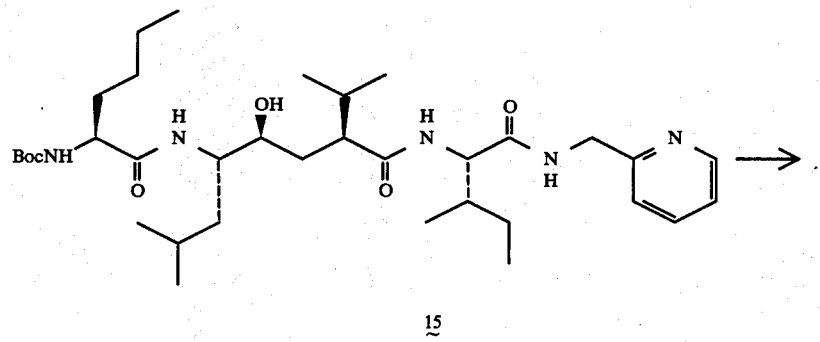
15
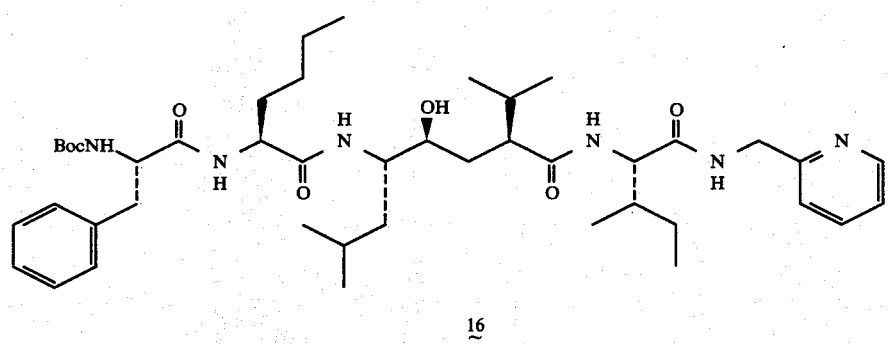
16
Scheme V
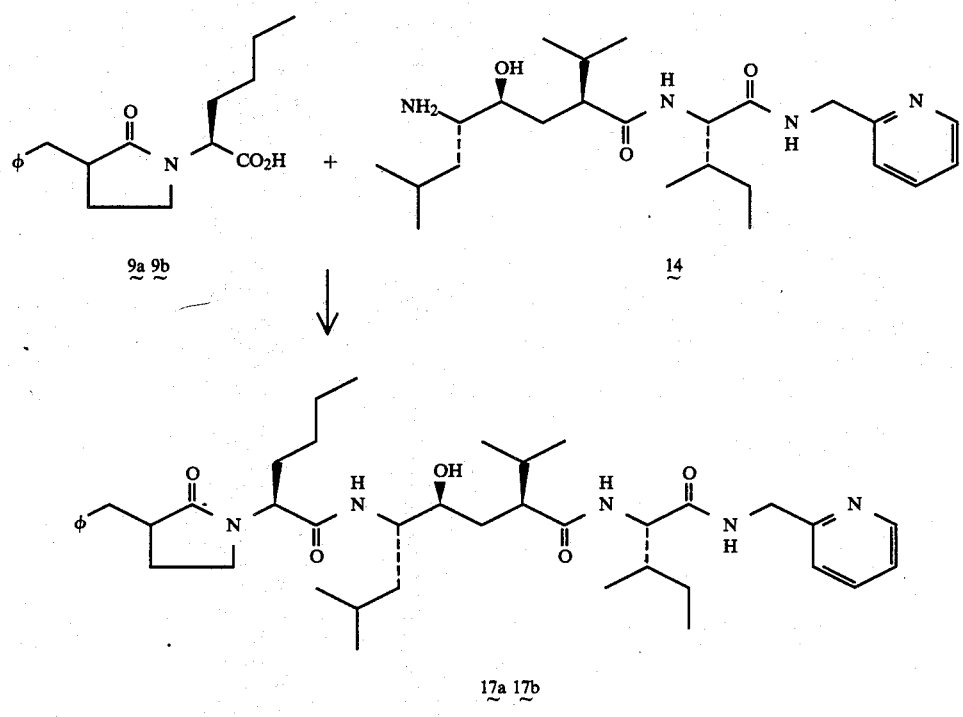

Scheme VI
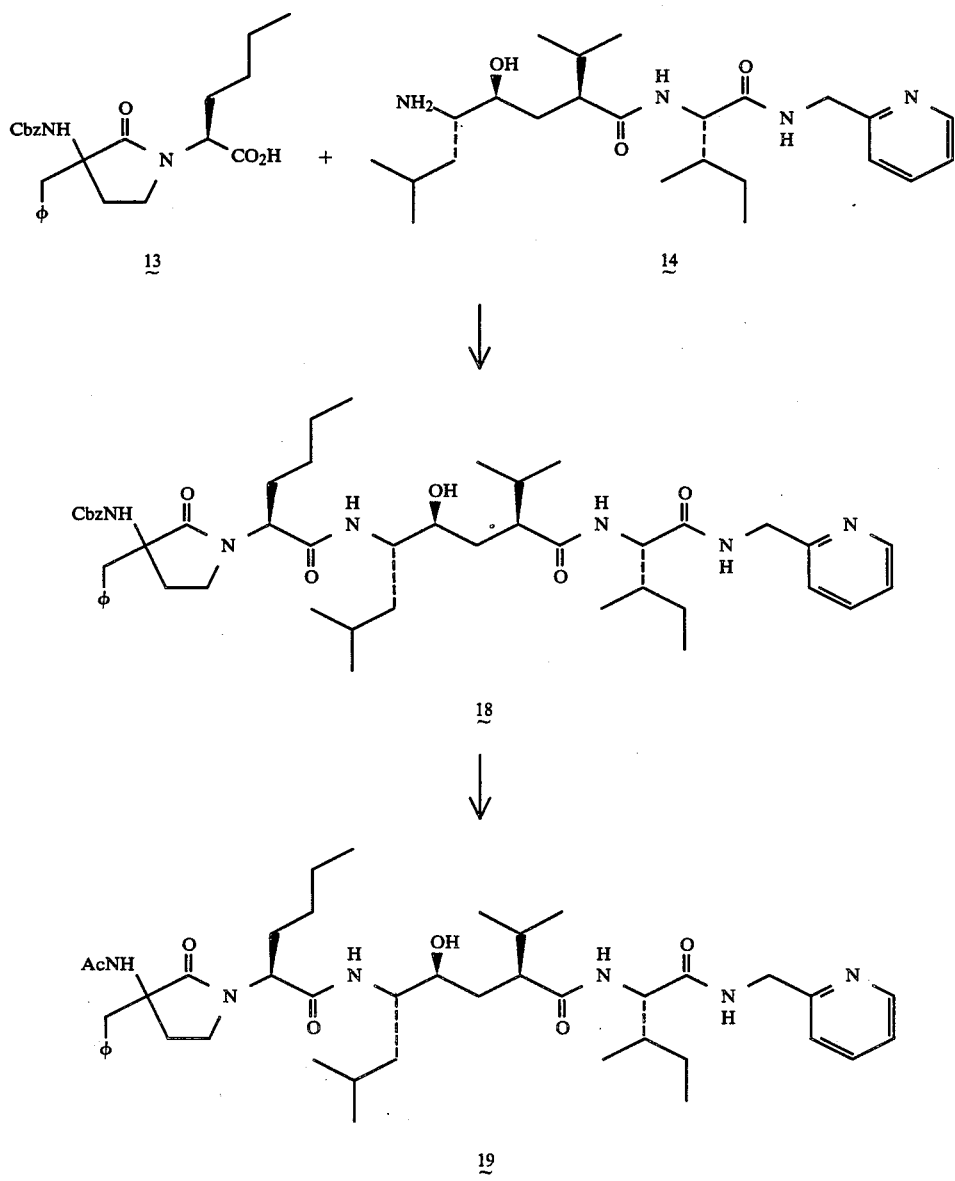
Scheme VII
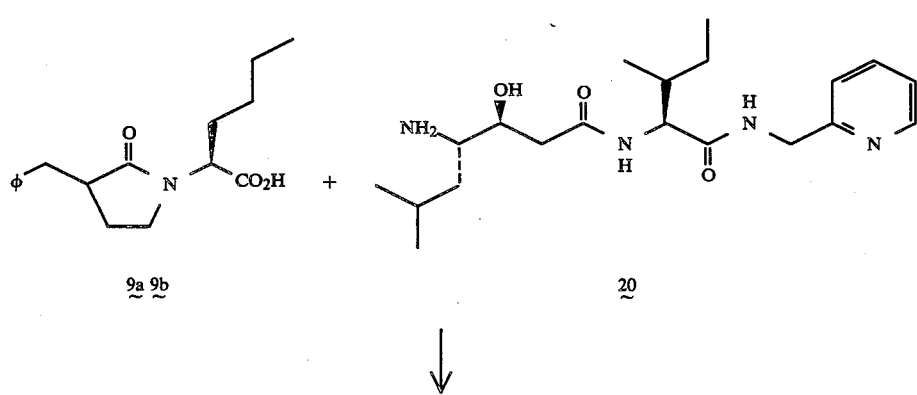

Scheme VII
-continued

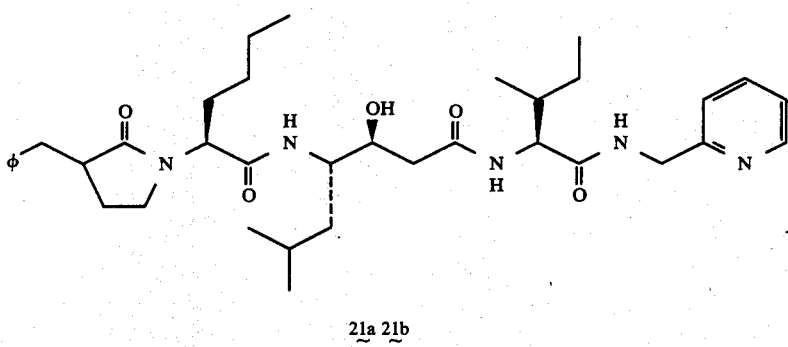

21a 21b

I claim:
1. A renin inhibitory peptide of the formula
X—$A_6$—$B_7$—$C_8$—$D_9$—$E_{10}$—$F_{11}$—$G_{12}$—$H_{13}$—$I_{14}$—Z,
wherein X is
(a) hydrogen,
(b) $C_1$-$C_5$alkyl
(c) $R_5$—O—$CH_2$—C(O)—,
(d) $R_5$—$CH_2$—O—C(O)—,
(e) $R_5$—O—C(O)—,
(f) $R_5$—$(CH_2)_n$—C(O)—,
(g) $R_4N(R_4)$—$(CH_2)_n$—C(O)—,
(h) $R_5$—$SO_2$—$(CH_2)_q$—C(O)—,
(i) $R_5$—$SO_2$—$(CH_2)_q$—O—C(O)—, or
(j) $R_6$—$(CH_2)_i$—C(O)—;
wherein $A_6$ is absent or a divalent moiety of the formula $XL_1$, $XL_2$, or $XL_{2a}$

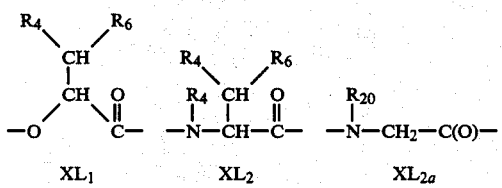

wherein $B_7$ is absent or a divalent moiety of the formula $XL_b$

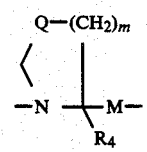

wherein $C_8$—$D_9$ is $XL_3$ or $XL_{3a}$, or

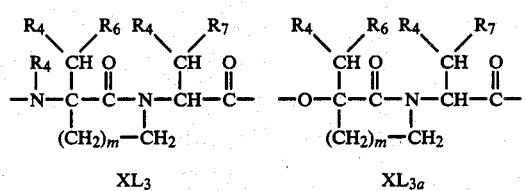

wherein $C_8$—$D_9$ is a monovalent moiety of the formula $XL_{3b}$ when X, $A_6$, and $B_7$ are absent;

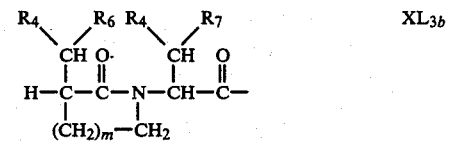

wherein $E_{10}$—$F_{11}$ is a divalent moiety of the formula $XL_6$, $XL_{6a}$, $XL_{6b}$, $XL_{6c}$, $XL_{6d}$ or $XL_{6e}$;

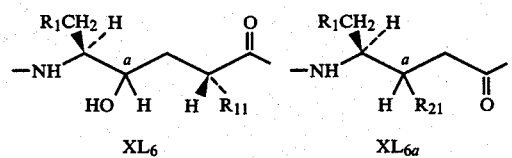

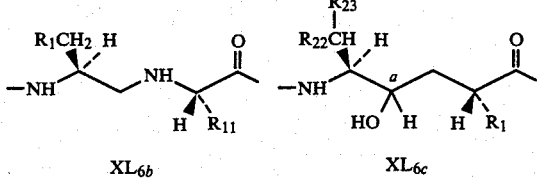

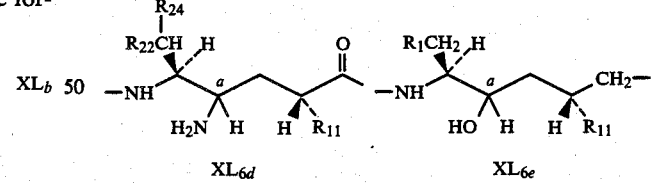

wherein * indicates an asymmetric center which is either in the R or S configuration;
wherein $G_{12}$ is absent or a divalent moiety of the formula $XL_4$ or $XL_{4a}$;

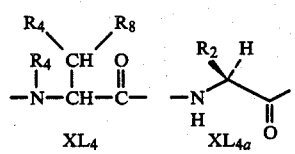

wherein $H_{13}$ is absent or a divalent moiety of the formula $XL_4$;

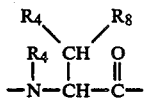
XL4 wherein I14 is absent or a divalent moiety of the formula XL5;

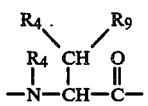
XL5 wherein Z is
(a) —O—$R_{10}$,
(b) —N($R_4$)$R_{14}$, or
(c) $C_4$-$C_8$cyclic amino;
wherein R is
(a) isopropyl,
(b) isobutyl,
(c) phenylmethyl, or
(d) $C_3$-$C_7$cycloalkyl;
wherein $R_1$ is
(a) hydrogen,
(b) $C_1$-$C_5$alkyl,
(c) aryl,
(d) $C_3$-$C_7$cycloalkyl,
(e) —Het,
(f) $C_1$-$C_3$alkoxy, or
(g) $C_1$-$C_3$alkylthio;
wherein $R_2$ is
(a) hydrogen, or
(b) —CH($R_3$)$R_4$;
wherein $R_3$ is
(a) hydrogen,
(b) hydroxy,
(c) $C_1$-$C_5$alkyl,
(d) $C_3$-$C_7$cycloalkyl,
(e) aryl,
(f) —Het,
(g) $C_1$-$C_3$alkoxy, or
(h) $C_1$-$C_3$alkylthio;
wherein $R_4$ at each occurrence is the same or different and is
(a) hydrogen, or
(b) $C_1$-$C_5$alkyl;
wherein $R_5$ is
(a) $C_1$-$C_6$alkyl,
(b) $C_3$-$C_7$cycloalkyl,
(c) aryl,
(d) —Het, or
(e) 5-oxo-2-pyrrolidinyl;
wherein $R_6$ is
(a) hydrogen,
(b) $C_1$-$C_5$alkyl,
(c) —(CH$_2$)$_p$—aryl,
(d) —(CH$_2$)$_p$—Het,
(e) —(CH$_2$)$_p$—$C_3$-$C_7$cycloalkyl,
(f) 1- or 2-adamantyl,
(g) —S—aryl,
(h) —S—$C_3$-$C_7$cycloalkyl, or
(i) —S—$C_1$-$C_6$—alkyl;
wherein $R_7$ is
(a) hydrogen,
(b) $C_1$-$C_5$alkyl,
(c) hydroxy,
(d) amino $C_1$-$C_4$alkyl—,
(e) guanidinyl $C_1$-$C_3$alkyl—,
(f) aryl,
(g) —Het,
(h) methylthio,
(i) —(CH$_2$)$_p$—$C_3$-$C_7$cycloalkyl, or
(j) amino;
wherein $R_8$ is
(a) hydrogen,
(b) $C_1$-$C_5$alkyl,
(c) hydroxy,
(d) aryl,
(e) —Het,
(f) guanidinyl $C_1$-$C_3$alkyl—, or
(g) —(CH$_2$)$_p$—$C_3$-$C_7$cycloalkyl;
wherein $R_9$ is
(a) hydrogen,
(b) hydroxy,
(c) amino $C_1$-$C_4$alkyl—, or
(d) guanidinyl $C_1$-$C_3$alkyl—;
wherein $R_{10}$ is
(a) hydrogen,
(b) $C_1$-$C_5$alkyl,
(c) —(CH$_2$)$_n$$R_{16}$,
(d) —(CH$_2$)$_n$$R_{17}$,
(e) $C_3$-$C_7$cycloalkyl,
(f) a pharmaceutically acceptable cation,
(g) —CH($R_{25}$)—CH$_2$—$R_{15}$, or
(h) —CH$_2$—CH($R_{12}$)—$R_{15}$;
wherein $R_{11}$ is —R or —$R_2$;
wherein $R_{12}$ is —(CH$_2$)$_n$—$R_{13}$;
wherein $R_{13}$ is
(a) aryl,
(b) amino,
(c) mono-, di or tri-$C_1$-$C_3$alkylamino,
(d) —Het,
(e) $C_1$-$C_5$alkyl
(f) $C_3$-$C_7$cycloalkyl,
(g) $C_2$-$C_5$alkenyl,
(h) $C_3$-$C_7$cycloalkenyl,
(i) hydroxy,
(j) $C_1$-$C_3$alkoxy,
(k) $C_1$-$C_3$alkanoyloxy,
(l) mercapto,
(m) $C_1$-$C_3$alkylthio,
(n) —COOH,
(o) —CO—O—$C_1$-$C_6$alkyl,
(p) —CO—O—CH$_2$—($C_1$-$C_3$alkyl)—N($C_1$-$C_3$alkyl)$_2$,
(q) —CO—NR$_{22}$R$_{26}$;
(r) $C_4$-$C_7$cyclic amino,
(s) $C_4$-$C_7$cycloalkylamino,
(t) guanidyl,
(u) cyano,
(v) N-cyanoguanidyl,
(w) cyanoamino,
(x) (hydroxy $C_2$-$C_4$alkyl)amino, or
(y) di-(hydroxy$C_2$-$C_4$alkyl)amino;
wherein $R_{14}$ is
(a) hydrogen,
(b) $C_1$-$C_{10}$alkyl,
(c) —(CH$_2$)$_n$—$R_{18}$,
(d) —(CH$_2$)$_n$—$R_{19}$,
(e) —CH($R_{25}$)—CH$_2$—$R_{15}$,
(f) —CH$_2$—CH($R_{12}$)—$R_{15}$,
(g) (hydroxy $C_1$-$C_8$alkyl), or
(h) ($C_1$-$C_3$alkoxy)$C_1$-$C_8$alkyl;
wherein $R_{15}$ is (a) hydroxy,
(b) $C_3$-$C_7$cycloalkyl,
(c) aryl,
(d) amino,
(e) mono-, di-, or tri-$C_1$-$C_3$alkylamino,
(f) mono- or di-[hydroxy $C_2$-$C_4$alkyl]amino,
(g) —Het,
(h) $C_1$-$C_3$alkoxy—,
(i) $C_1$-$C_3$alkanoyloxy—,
(j) mercapto,
(k) $C_1$-$C_3$alkylthio—,
(l) $C_1$-$C_5$alkyl,
(m) $C_4$-$C_7$cyclic amino,
(n) $C_4$-$C_7$cycloalkylamino,
(o) $C_1$-$C_5$alkenyloxy,
(p) $C_3$-$C_7$cycloalkenyl;
wherein $R_{16}$ is
(a) aryl,
(b) amino,
(c) mono- or di-$C_1$-$C_3$alkylamino,
(d) hydroxy,
(e) $C_3$-$C_7$cycloalkyl,
(f) $C_4$-$C_7$cyclic amino, or
(g) $C_1$-$C_3$alkanoyloxy;
wherein $R_{17}$ is
(a) —Het,
(b) $C_2$-$C_5$alkenyl,
(c) $C_3$-$C_7$cycloalkenyl,
(d) $C_1$-$C_3$alkoxy,
(e) mercapto,
(f) $C_1$-$C_3$alkylthio,
(g) —COOH,
(h) —CO—O—$C_1$-$C_6$alkyl,
(i) —CO—O—$CH_2$—($C_1$-$C_3$alkyl)—N($C_1$-$C_3$alkyl)$_2$,
(j) —CO—NR$_{22}$R$_{26}$,
(k) tri-$C_1$-$C_3$alkylamino,
(l) guanidyl,
(m) cyano,
(n) N-cyanoguanidyl,
(o) (hydroxy $C_2$-$C_4$alkyl)amino,
(p) di-(hydroxy $C_2$-$C_4$alkyl)amino, or
(q) cyanoamino;
wherein $R_{18}$ is
(a) amino,
(b) mono-, or di-$C_1$-$C_3$alkylamino,
(c) $C_4$-$C_7$cyclic amino; or
(d) $C_4$-$C_7$cycloalkylamino;
wherein $R_{19}$ is
(a) aryl,
(b) —Het,
(c) tri-$C_1$-$C_3$alkylamino,
(d) $C_3$-$C_7$cycloalkyl,
(e) $C_2$-$C_5$alkenyl,
(f) $C_3$-$C_7$cycloalkenyl,
(g) hydroxy,
(h) $C_1$-$C_3$alkoxy,
(i) $C_1$-$C_3$alkanoyloxy,
(j) mercapto,
(k) $C_1$-$C_3$alkylthio,
(l) —COOH,
(m) —CO—O—$C_1$-$C_6$alkyl,
(n) —CO—O—$CH_2$—($C_1$-$C_3$alkyl)—N($C_1$-$C_3$alkyl)$_2$,
(o) —CO—NR$_{22}$R$_{26}$,
(p) guanidyl,
(q) cyano,
(r) N-cyanoguanidyl,
(s) cyanoamino,
(t) (hydroxy $C_2$-$C_4$alkyl)amino,
(u) di-(hydroxy $C_2$-$C_4$alkyl)amino; or
(v) —SO$_3$H;
wherein $R_{20}$ is
(a) hydrogen,
(b) $C_1$-$C_5$alkyl, or
(c) aryl—$C_1$-$C_5$alkyl;
wherein $R_{21}$ is
(a) —NH$_2$, or
(b) —OH;
wherein $R_{22}$ is
(a) hydrogen, or
(b) $C_1$-$C_3$alkyl;
wherein $R_{23}$ is
(a) —(CH$_2$)$_n$—OH,
(b) —(CH$_2$)$_n$—NH$_2$,
(c) aryl, or
(d) $C_1$-$C_3$alkyl;
wherein $R_{24}$ is
(a) —R$_1$,
(b) —(CH$_2$)$_n$—OH, or
(c) —(CH$_2$)$_n$—NH$_2$;
wherein $R_{25}$ is
(a) hydrogen,
(b) $C_1$-$C_3$alkyl, or
(c) phenyl—$C_1$-$C_3$alkyl;
wherein $R_{26}$ is
(a) hydrogen,
(b) $C_1$-$C_3$alkyl, or
(c) phenyl—$C_1$-$C_3$alkyl;
wherein m is one or two;
wherein for each occurrence n is independently an integer of zero to five, inclusive;
wherein p is zero to 2 inclusive;
wherein q is 1 to 5, inclusive;
wherein Q is
(a) —CH$_2$—,
(b) —CH(OH)—,
(c) —O—, or
(d) —S—; and
wherein M is
(a) —CO—, or
(b) —CH$_2$—;
wherein aryl is phenyl or naphthyl substituted by zero to 3 of the following:
(a) $C_1$-$C_3$alkyl,
(b) hydroxy,
(c) $C_1$-$C_3$alkoxy,
(d) halo,
(e) amino,
(f) mono- or di-$C_1$-$C_3$alkylamino,
(g) —CHO,
(h) —COOH,
(i) COOR$_{26}$,
(j) CONHR$_{26}$,
(k) nitro,
(l) mercapto,
(m) $C_1$-$C_3$alkylthio,
(n) $C_1$-$C_3$alkylsulfinyl,
(o) $C_1$-$C_3$alkylsulfonyl,
(p) —N(R$_4$)—$C_1$-$C_3$alkylsulfonyl,
(q) SO$_3$H,
(r) SO$_2$NH$_2$,
(s) —CN, or
(t) —CH$_2$NH$_2$;
wherein —Het is a 5- or 6-membered saturated or unsaturated ring containing from one to three heteroatoms selected from the group consisting of nitrogen, oxygen, and sulfur; and including any bicyclic group in which any of the above heterocyclic rings is fused to a benzene ring, which heterocyclic moiety is substituted with zero to 3 of the following:
(i) $C_1$-$C_6$alkyl,
(ii) hydroxy,
(iii) trifluoromethyl,
(iv) $C_1$-$C_4$alkoxy,
(v) halo,
(vi) aryl,
(vii) aryl $C_1$-$C_4$alkyl—,
(viii) amino,
(ix) mono- or di-$C_1$-$C_4$alkylamino, and
(x) $C_1$-$C_5$alkanoyl;

with the overall provisos that
(1) $R_{18}$ or $R_{19}$ is hydroxy, mercapto, or amino, or a mono-substituted nitrogen containing group bonded through the nitrogen only when n is not one;
(2) $R_{12}$ is —$(CH_2)_n$—$R_{13}$ and n is zero and both $R_{13}$ and $R_{15}$ are oxygen-, nitrogen-, or sulfur-containing substituents bonded through the hetero atom, only when the hetero atom is not also bonded to hydrogen;
(3) $R_{17}$ or $R_{19}$ is —COOH only when n for that moiety is other than zero;
(4) $R_{16}$ or $R_{17}$ is an amino-containing substituent, hydroxy, mercapto, or —Het bonded through the hetero atom only when n for that substituent is an integer from two to five, inclusive;
(5) when $R_{12}$ is —$(CH_2)_n$—$R_{13}$ and n is zero, then $R_{13}$ and $R_{15}$ cannot both be —COOH; and
(6) $R_{17}$ or $R_{19}$ is —Het, only when —Het is other than cyclic amino;
or a carboxy-, amino-, or other reactive group-protected form thereof;
or a pharmaceutically acceptable acid addition salt thereof.

2. 3R-Benzyl-2-oxo-1-pyrrolidine-2S-hexanoyl-5S-amino-4S-hydroxy-2S-isopropyl-7-methyl-octanoyl-L-isoleucyl-2-pyridylmethylamide, a compound of claim 1.

3. 3S-Benzyl-2-oxo-1-pyrrolidine-2S-hexanoyl-5S-amino-4S-hydroxy-2S-isopropyl-7-methyl-octanoyl-L-isoleucyl-2-pyridylmethylamide, a compound of claim 1.

4. (R and S)-3-benzyl-3-benzyloxycarbonylamino-2-oxo-1-pyrrolidine-2S-hexanoyl-5S-amino-4S-hydroxy-2S-isopropyl-7-methyl-octanoyl-L-isoleucyl-2-pyridylmethylamide, a compound of claim 1.

5. (R and S)-3-benzyl-3-acetylamino-2-oxo-1-pyrrolidine-2S-hexanoyl-5S-amino-4S-hydroxy-2S-isopropyl-7-methyl-octanoyl-L-isoleucyl-2-pyridylmethylamide, a compound of claim 1.

6. 3R-Benzyl-2-oxo-1-pyrrolidine-2S-hexanoyl-4S-amino-3S-hydroxy-6-methyl-heptanoyl-L-isoleucyl-2-pyridylmethylamide, a compound of claim 1.

7. 3S-Benzyl-2-oxo-1-pyrrolidine-2S-hexanoyl-4S-amino-3S-hydroxy-6-methyl-heptanoyl-L-isoleucyl-2-pyridylmethylamide, a compound of claim 1.

* * * * *

UNITED STATES PATENT OFFICE
CERTIFICATE OF CORRECTION

Patent No. __4,705,846__   Dated __10 November 1987__

Inventor(s) __S. Thaisrivongs__

It is certified that error appears in the above-identified patent and that said Letters Patent are hereby corrected as shown below:

Column 1, lines 23-24: "-Leu" should read -- ↓Leu --.
Column 1, lines 35-36: "-Val" should read -- ↓Val --.
Column 1, line 51: "disclosed" should read --disclose--.
Column 4, line 49: "$C_1$-$C_7$" should read --$C_4$-$C_7$--.
Column 5, line 59: "$NH_2$," should read --$NH_2$;--.
Column 7, line 30: "atoms" should read --atom--.
Column 7, line 43: "-dietyl" should read -- -diethyl--.
Column 7, line 48: "ary" should read --aryl--.
Column 7, line 65: "theinyl" should read --thienyl--.
Column 8, line 28: "Symbolish" should read --Symbolism--.
Column 10, line 51: "Chung" should read --Cheung--.
Column 12, line 45: "phae" should read --phase--.
Column 12, line 68: "MS M/Z" should read --MS: M/Z--.
Column 13, line 26: "thioethy" should read --thioethyl--.
Column 15, line 32: "$[\delta]_D$" should read --$[\alpha]_D$--.
Column 26, line 34 ($XL_6$ and $XL_{6a}$) should read:

   

UNITED STATES PATENT OFFICE
CERTIFICATE OF CORRECTION

Patent No. 4,705,846  Dated 10 November 1987

Inventor(s) S. Thaisrivongs

It is certified that error appears in the above-identified patent and that said Letters Patent are hereby corrected as shown below:

Column 26, lines 43-44 should read:

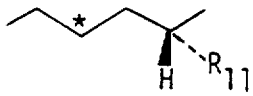

Column 26, line 50 ($XL_{6d}$ and $XL_{6e}$) should read:

Signed and Sealed this

Twenty-seventh Day of September, 1988

Attest:

DONALD J. QUIGG

Attesting Officer  Commissioner of Patents and Trademarks

UNITED STATES PATENT OFFICE
CERTIFICATE OF CORRECTION

Patent No. 4,705,846          Dated 10 November 1987

Inventor(s) S. Thaisrivongs

It is certified that error appears in the above-identified patent and that said Letters Patent is hereby corrected as shown below:

Column 2, line 34:
"(j) $R_6-(CH_2)_i-C(O)-;$" should read: --(j) $R_6-CH_2-C(O)-;$--

Column 25, line 34:
"(j) $R_6-(CH_2)_i-C(O)-;$" should read: --(j) $R_6-CH_2-C(O)-;$--

Signed and Sealed this

Fifth Day of February, 199

Attest:

HARRY F. MANBECK, JR.

Attesting Officer     Commissioner of Patents and Trademarks